US012558204B1

(12) United States Patent
Lowthorp et al.

(10) Patent No.: US 12,558,204 B1
(45) Date of Patent: Feb. 24, 2026

(54) APPARATUS AND METHOD FOR MANUFACTURING A DENTAL MILLING BLOCK WITH A GRADUATED COLOR AND/OR TRANSLUCENCY PROFILE

(71) Applicant: The Argen Corporation, San Diego, CA (US)

(72) Inventors: Jeffery Lowthorp, Oceanside, CA (US); Carlos Sanchez, La Jolla, CA (US)

(73) Assignee: The Argen Corporation, San Diego, CA (US)

( * ) Notice: Subject to any disclaimer, the term of this patent is extended or adjusted under 35 U.S.C. 154(b) by 0 days.

(21) Appl. No.: 19/062,719

(22) Filed: Feb. 25, 2025

(51) Int. Cl.
*A61K 6/818* (2020.01)
*A61C 13/00* (2006.01)
*A61C 13/08* (2006.01)

(52) U.S. Cl.
CPC ........ *A61C 13/081* (2013.01); *A61C 13/0022* (2013.01); *A61K 6/818* (2020.01)

(58) Field of Classification Search
CPC ............................ A61C 13/0022; A61K 6/818
See application file for complete search history.

(56) References Cited

U.S. PATENT DOCUMENTS

| | | | | |
|---|---|---|---|---|
| 5,219,805 | A | * | 6/1993 | Yoshida .............. C04B 41/5023 |
| | | | | 501/103 |
| 5,263,858 | A | * | 11/1993 | Yoshida ................ C04B 35/486 |
| | | | | 433/8 |
| 8,697,176 | B2 | | 4/2014 | Wang et al. |
| 8,936,848 | B2 | | 1/2015 | Jung et al. |
| 10,245,127 | B2 | | 4/2019 | Kim et al. |
| 11,998,408 | B2 | * | 6/2024 | Goetzinger ............. B28B 11/24 |
| 2007/0197368 | A1 | * | 8/2007 | Tsukuma .................. A61C 7/14 |
| | | | | 501/103 |
| 2010/0062396 | A1 | * | 3/2010 | Hock ..................... C04B 35/505 |
| | | | | 433/201.1 |
| 2015/0315086 | A1 | * | 11/2015 | Kawamura ........... C04B 35/486 |
| | | | | 501/134 |
| 2016/0332918 | A1 | * | 11/2016 | Carden ............. C04B 35/62625 |
| 2017/0273764 | A1 | * | 9/2017 | Volkl ..................... A61C 13/09 |
| 2018/0263863 | A1 | * | 9/2018 | Kim ........................ C04B 41/52 |
| 2019/0099244 | A1 | * | 4/2019 | Vollmann ............. A61C 13/083 |
| 2022/0183804 | A1 | * | 6/2022 | Fecher ................... A61K 6/822 |
| 2022/0184847 | A1 | * | 6/2022 | Fecher ................... A61K 6/813 |
| 2023/0338123 | A1 | * | 10/2023 | Jahns ................. C04B 38/0058 |
| 2024/0033186 | A1 | * | 2/2024 | Niwa ................ C04B 35/62625 |
| 2024/0050204 | A1 | * | 2/2024 | Li ........................... B32B 18/00 |

FOREIGN PATENT DOCUMENTS

EP          31088490 B1     4/2019

* cited by examiner

*Primary Examiner* — Andrew D Graham
(74) *Attorney, Agent, or Firm* — Nicola A. Pisano; Cozen O'Connor

(57)          ABSTRACT

Apparatus and processes by providing for gradually interleaving layers of zirconia powders having different concentrations of colorants and yttria to obtain color and translucency gradients that more closely mimic natural teeth, in which apparatus includes a comb having a multiplicity of tines that is extended vertically into a mold configured to hold at least two layers of differently constituted powders, such that adjacent layers of the powders form an interface. The comb is reciprocated to create a textured surface pattern on a topmost layer of powder and additionally may be used to penetrate an interface between adjacent layers, thereby redistributing the particles near the interface.

17 Claims, 5 Drawing Sheets

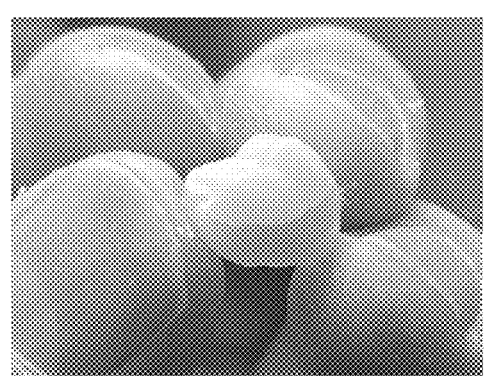
FIG. 1A
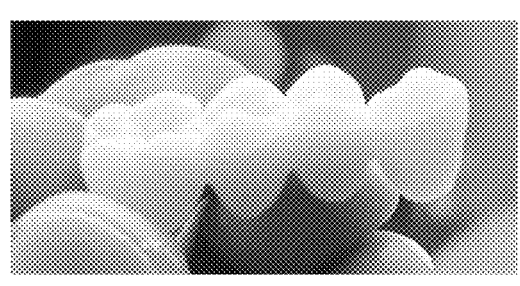
FIG. 1B
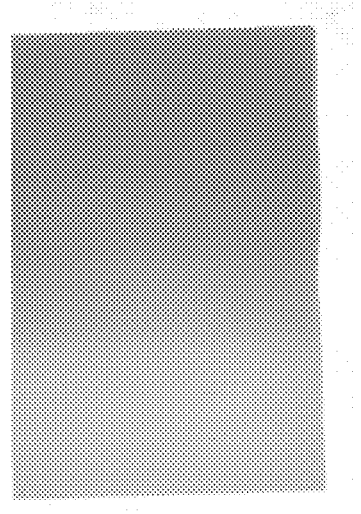
FIG. 2
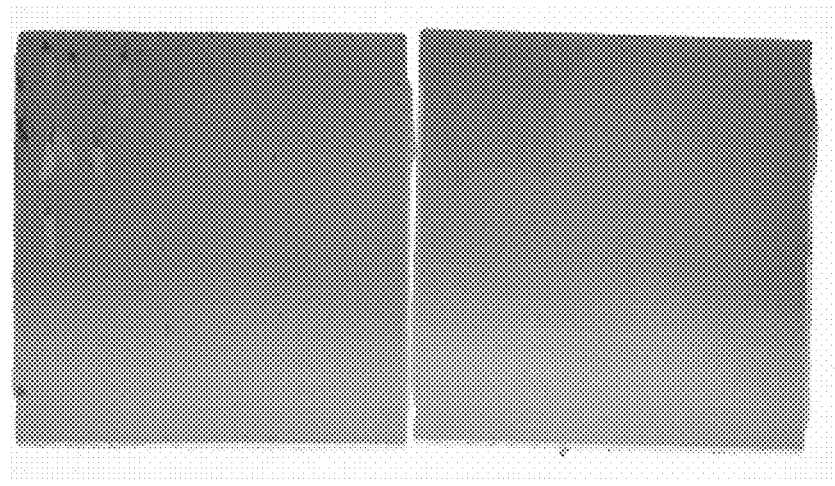
FIG. 3                     FIG. 4

APPARATUS AND METHOD FOR MANUFACTURING A DENTAL MILLING BLOCK WITH A GRADUATED COLOR AND/OR TRANSLUCENCY PROFILE

FIELD OF THE INVENTION

The invention relates to a process of manufacturing a dental milling block, for use in making highly aesthetic dental restorations, having a graduated color and/or translucency profile that mimics natural tooth translucency gradients.

BACKGROUND OF THE INVENTION

Zirconia (ZrO$_2$) powders are available from a variety of manufacturers that can be used to create milling blocks for dental restorations having translucency variations from gingival to incisal areas that mimic natural teeth. Commercially available powders typically include different amounts of yttria (Y$_2$O$_3$) or colorant, which may be used to provide different degrees of translucency or color shades across the height of a milling block. One challenge attempting to mimic natural tooth coloring and translucency gradients is the ability to blend adjacent layers of powder so as to achieve a natural appearance.

Different approaches are described in previously known patents for producing dental milling blocks having realistic color and translucency gradients. For example, it is known that color and/or translucency variations across the height of a milling block or milled prosthesis can be obtained by dipping the zirconia block or pre-sintered prosthesis in liquids containing varying amounts of colorants or yttria solutions, such that a gradient is created by the coloring or yttria ions being absorbed by the porous dental milling block.

For example, Chinese patent CN 104909745B, assigned to Chengdu Besmile Biotechnology Co., Ltd. describes a method to obtain uniform gradient-color zirconium oxide blocks comprising steps of: (1) weighing raw materials such as cerium dioxide, iron oxide, zirconia, yttria and other oxides of rare-earth materials; (2) adding a polymer binder and granulating; (3) shaping the granulated material; (4) carrying out isostatic pressing; (5) pre-sintering the blanks; and (6) placing the pre-sintered blanks in a container containing coloring solutions. The colored blanks then are sintered to obtain blanks having a uniform color gradient for use in creating dental restorations. Chinese published patent application CN 108585845A, assigned to Changsha Peng Deng Biological Ceramics Co. Ltd., describes a similar process for infusing zirconium oxide blanks with varying amounts of soluble yttrium and color solutions to obtain color and translucency gradients in the milling blanks. U.S. Patent Publication No. 2019/0233340 A1, assigned to James R Glidewell Dental Ceramics Inc., describes a similar method of infusing materials into zirconia milling blanks. A drawback common to these approaches is complexity, in that the pre-sintered block must be processed through a series of coloring and infusion steps, which add time and cost to the manufacturing process and also may result in non-uniform results between blank batches.

Another previously known process for obtaining milling blanks with color and/or translucency variations involves layering differently constituted powder compositions one over the other and compacting the powder composition afterwards. For example, European Patent EP 3 108 849 B1, assigned to Solventum Intellectual Properties Co., describes a porous multi-layered colored zirconia dental mill blank having comprising two different layers arranged in alternating order, wherein the thickness of the individual layers of one composition decreasing from bottom to top and the thickness of the individual layers with the other composition decreasing from top to bottom.

Similarly, U.S. Pat. No. 10,245,127 B2, assigned to Dental Max Co., Ltd., describes a method of manufacturing a multilayer zirconia block for dental restorations, including multiple material mixing steps, followed by a compression molding step, and a calcination step. The patent describes that the multilayer zirconia blank contains yttrium oxide, the amount of which is adjusted in the manufacturing process, to achieve color and translucency similar to that of natural teeth after application of a coloring solution.

A further manufacturing process described in previously known patents involves the use of a mixer for mixing powder compositions. For example, U.S. Pat. No. 10,441, 391, assigned to Dentsply Sirona Inc., describes a method of manufacturing a colored zirconia blank in which raw materials are mixed in powder form, and the resulting mixture pressed in a mold and sintered. One of the powder mixtures contains a colorant, such that after introduction of a first powder layer, another material having less colorant is deposited in the mold to form an intermediate layer that mixes with the first layer. A further layer may be deposited in the mold that has a higher concentration of yttrium oxide content than the first layer.

U.S. Pat. No. 10,219,880, assigned to Solventum Intellectual Properties Co., describes dental milling blocks having different layers or regions, including a first layer of a first hard restorative material having a first translucency and a first shade, and a second layer of a second hard restorative material having a second translucency and a second shade. The first and second layers form an interface having a first curvature across a first plane of symmetry of the dental mill blank. U.S. Pat. No. 10,028,809, assigned to 3M Innovative Properties Co., describes a porous dental milling block having at least two geometrically defined material that respectively contain different amounts of tetragonal crystal phases and cubic zirconia crystal phases. U.S. Pat. No. 11,998,408, assigned to Solventum Intellectual Properties Co., describes apparatus for mixing adjacent layers of differently constituted powders by inserting a rotating element that attempts to create a gradient between the powders.

A significant drawback of the processes described in the above-mentioned patents is that the resulting milling blanks exhibit either an unnaturally abrupt change at the interface (s) between adjacent layers or obtain an unnatural distribution of particles exhibiting different translucencies, may may result in speckling of the finished dental restorations.

In view of the foregoing, there is a need for apparatus and methods for gradually interleaving adjacent layers of the multi-layered zirconia milling blank that provide a natural gradient in color and translucency of the finished dental restorations that are simple to use, cost-effective and avoid the drawbacks of previously known techniques.

SUMMARY OF THE INVENTION

The present invention overcomes the complexity and disadvantageous results of previously known apparatus and processes by providing apparatus and methods for gradually interleaving layers of zirconia powders having different concentrations of colorants and yttria to obtain color and translucency gradients that more closely mimic natural teeth.

In accordance with one aspect of the invention, apparatus includes a comb having a multiplicity of tines that is extended vertically into a mold configured to hold at least two layers of differently constituted powders, such that adjacent layers of the powders form an interface. The comb is reciprocated for at least one cycle to create a textured surface pattern on a topmost layer of powder and may be used additionally to penetrate an interface between adjacent layers to cause interleaving of the two layers and redistribute the particles near the interface. In this manner, a natural-looking color and translucency gradient is created in the sintered milling block, and ultimately the dental restoration milled therefrom.

In a preferred embodiment of manufacturing a dental milling block, a mold is provided that has a cavity with thickness in a z-direction and an area in an x/y-plane, and a comb having a multiplicity of tines configured to be recip-rocated in the z-direction to extend vertically into the mold. During a milling blank creation process, a first layer of a zirconia powder having a first concentration of yttria, and optionally, a first concentration of a colorant, is deposited in the mold cavity. The top surface of the first layer, i.e., that is not in contact with the bottom of the mold cavity, may be leveled, e.g., using a spatula, slight compression or by agitation. The comb then is extended into the mold so that only shaped end portions of the tines extend into the top surface to create a regular textured pattern, e.g., having a multiplicity of dimples. A second layer of zirconia powder having a second concentration of yttria, and optionally, a second concentration of colorant then is deposited in the mold on top of the first layer, such that the top surface of the first layer and the bottom surface of the second layer form a complimentary and interlocking textured interface. The top surface of the second layer also may be leveled using a spatula, compression, or agitation and then the comb advanced to create a textured pattern on the topmost layer.

Further in accordance with the invention, the comb is inserted vertically downward into the mold to the penetrate the interface between the adjacent layers, and withdrawn, thereby intermixing the particles of the respective powders at the interface. Insertion and retraction of the comb through the interface may be repeated several times, with the inser-tion depth of the comb for each penetration being the same, or more preferably, shallower, to thereby redistribute the powders to a lesser extent relative to the original interface during each subsequent penetration. Once this process is completed, the mold may be subjected to further isostatic compression and sintered to form a milling blank from which dental restorations may be prepared.

In accordance with another aspect of the invention, the comb of the apparatus may include tines having shaped end portions that facilitates mixing at the interface. In a preferred embodiment, the shaped end portion may have a conical or conical-cruciform shape. Alternatively, the shaped end por-tion may be bulbous, spherical or hook shaped, such that the end portion pushes first layer material contacting its lower end surface vertically downward during penetration while simultaneously dragging material from the second layer downward into the first layer along a shoulder formed where the shaped end portion joins the tine. In this way, particles from the first and second layers may be interspersed any desired amount to affect the color and translucency across the vertical thickness of the milling blank, e.g., to attain color and translucency gradients that mimic gingival to incisal gradients in natural teeth. If desired, additional layers of differently constituted zirconia powder may be deposited atop the second and subsequent layers, and additional interleaving of the second layer and immediately adjacent layers may be achieved as described above.

In accordance with a further aspect of the invention, the comb may be reciprocated into the mold to interleave the first and second layers at least two times, with the comb being circumferentially rotated 90 degrees after being extracted during the first penetration cycle, thereby more thoroughly distributing the interleaving circumferentially within the resulting milling blank.

Further features of the invention, its nature and various advantages will be more apparent from the accompanying drawings and detailed description of the preferred embodi-ments.

BRIEF DESCRIPTION OF THE DRAWINGS

Further features of the invention, its nature and various advantages will be more apparent from the accompanying drawings and the following detailed description of the preferred embodiments:

FIGS. 1A and 1B are photographs demonstrating how dental restorations prepared in accordance with previously known processes, using multiply layers of yttria containing zirconia powders, result in cracking along the interface of the layers due to differential densification during sintering.

FIG. 2 is a photograph of a section of a sintered article prepared in accordance with previously known processes, showing banding of translucency when using multiply layers of yttria containing zirconia powders without interleaving of the interfaces between adjacent powder layers.

FIG. 3 is a photograph of section of a sintered article made from a milling blank, for comparison purposes, prepared in accordance with a previously known process of layering zirconia powders having different yttria concentrations.

FIG. 4 is a photograph of a sintered article made from a milling blank prepared in accordance with the present inven-tion, in which particles in the vicinity of the interface between the layers have been interspersed.

DETAILED DESCRIPTION OF THE INVENTION

Figure 5:
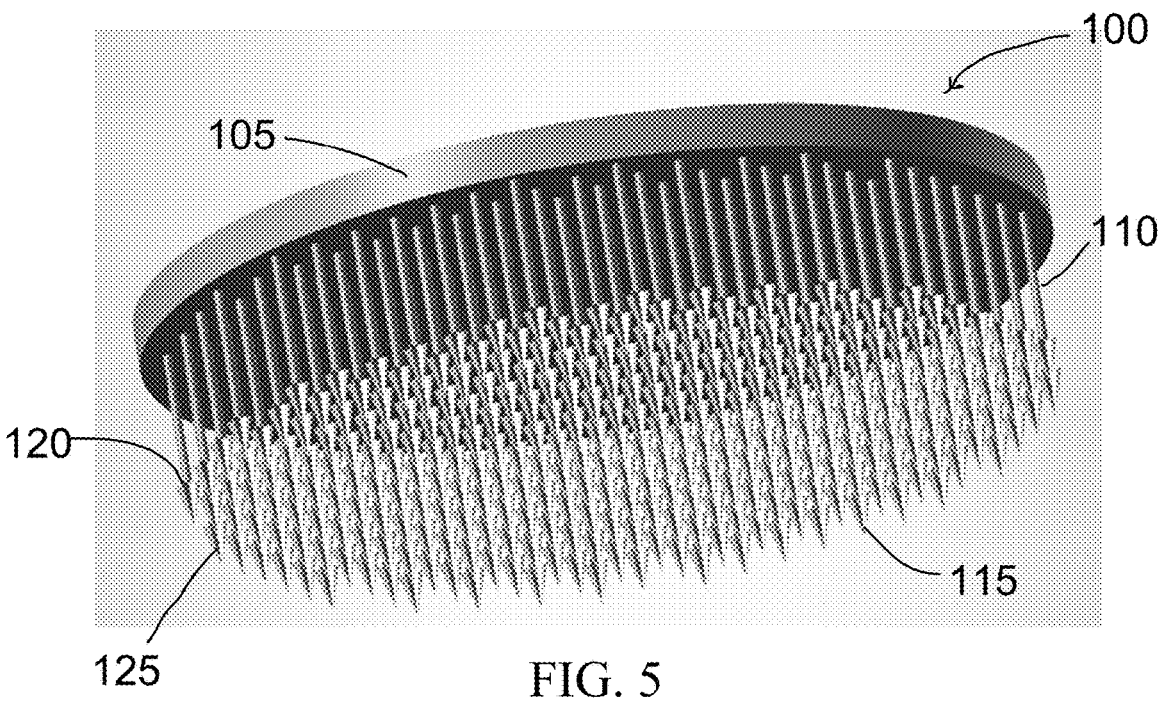
FIG. 5 is an exemplary embodiment of apparatus config-ured in accordance with the principles of the present inven-tion.

The present invention relates generally to apparatus and methods for interleaving layers of zirconia powders having different concentrations of colorants and yttria to obtain color and translucency gradients that more closely mimic natural teeth. As disclosed herein, the invention overcomes the complexity and disadvantageous artifacts arising from use of previously known apparatus and processes. In particular, a preferred embodiment of the apparatus of the present invention is a comb having a multiplicity of tines configured to create a regular textured interface during deposition of adjacent layers of differently constituted zirconia powders. Additionally, the comb may be reciprocated for at least one cycle to penetrate the interface between adjacent powders, there causing interleaving of the two layers and redistributing the particles in the vicinity of the interface to provide a natural-looking color and translucency gradient in the sintered milling block, and ultimately the dental restoration milled therefrom.

As used in this description and unless defined differently, the following terms shall have the below-specified meanings:

"Dental restoration" means an article which is to be used in the dental field to restore a defective tooth structure. The dental restoration typically has a 3-dimensional inner and outer surfaces that includes convex and concave structures, such that an outer surface typically has an overall convex shape, and an inner surface typically has an overall concave shape. The thickness of the dental restoration can vary from very thin, e.g., at the edges and rims (less than 0.1 mm) to thick, e.g., in the bite area (up to 8 or 16 mm). Sections bridging the crown portions in dental bridges might have a thickness up to 20 mm. Dental restorations described in herein comprises or essentially consist after sintering of a polycrystalline ceramic material of yttria stabilized zirconia. Examples of dental restorations include crowns (including monolithic crowns), bridges, inlays, onlays, veneers, facings, crown and bridged framework, abutments, orthodontic appliances (e.g., brackets, buccal tubes, cleats, and buttons), and parts thereof.

"Dental milling blank" means a solid block of material from which a dental restoration typically is to be machined in a subtractive process, e.g., milling, grinding, drilling etc. A dental milling blank generally has a defined geometric shape typically with two opposing flat surfaces.

"Ceramic" means an inorganic non-metallic material produced by application of heat. Ceramics are usually hard, porous, and brittle and, in contrast to glasses or glass ceramics, display an essentially purely crystalline structure.

"Mold" means a block with a hollow cavity intended to be filled with a material that can be compacted or solidified.

"Powder" means a dry, bulk material composed of particles that flow freely when shaken or tilted.

"Particle" means a substance being a solid having a shape, which may be regular or irregular, which can be geometrically determined. Particles typically may be analysed with respect to, e.g., size and size distribution.

"Density" means the ratio of mass to volume of an object. The unit of density is typically $g/cm^3$ and for an object may be calculated, e.g., by determining its volume (e.g., by calculation or applying the Archimedes principle or method) and measuring its mass. The volume of a sample can be determined based on the overall outer dimensions of the sample. The density of the sample may be calculated from the measured sample volume and the sample mass. The total volume of the material may be calculated from the mass of the sample and the density of the used material.

"Porous material" means a material comprising a partial volume that is formed by voids, pores, or cells in the technical field of ceramics.

"Sintering" or "firing" are used interchangeably and refers to heating a ceramic article to cause densification from a porous article to a higher density article. For zirconia-based ceramics a typical sintering temperature range is 1,100° C. to 1,600° C. In some cases, sintering also may include change of the material phase composition (for example, partial conversion of an amorphous phase toward a crystalline phase).

A dental zirconia article is classified as "pre-sintered", if the dental zirconia article has been treated with heat (temperature range of 900 to 1,100° C.) typically for 1 to 3 h to such an extent that the biaxial flexural strength of the dental ceramic measured according to the "punch on three ball test" ISO 6872:2015 is within a range of 8 to 80 MPa or 15 to 55 MPa. A pre-sintered dental ceramic usually has a porous structure and its density (usually about 3.0 $g/cm^3$ for an yttria stabilized zirconia ceramic) is less compared to a completely sintered dental ceramic framework (usually about 6.1 $g/cm^3$ for an yttria stabilized zirconia ceramic).

"Coloring ions" means ions which have an absorption in the spectral range visible to the human eye (e.g., 380 to 780 nm), which may result in a colored solution (visible to the human eye), if the coloring ions are dissolved in water (e.g., about 0.6 mol/l) and cause a coloring effect in the zirconia article that has been treated with a coloring solution and then sintered. Coloring ions also may be present (typically as component of a salt or oxide) in a powder before the powder, which is used for producing the zirconia article, is compacted.

"Machining" refers to milling, grinding, cutting, carving, or shaping a material by machine. Milling is usually faster and more cost effective than grinding. A "machinable article" is an article having a 3-dimensional shape and having sufficient strength to be machined.

A composition is "essentially or substantially free of" a certain component if the composition does not contain the component as an essential feature. Thus, the component is not intentionally added to the composition either as alone or in combination with other components or as an ingredient of another component. A composition that is essentially free of a certain component usually does not contain any of that component, except that a trace amount of the component may be present, e.g., due to impurities contained in the raw materials used.

As used herein, "a," "an," "the," "at least one" and "one or more" are used interchangeably. Also herein, the recitations of numerical ranges by endpoints include all numbers subsumed within that range (e.g., 1 to 5 includes 1, 1.5, 2, 2.75, 3, 3.80, 4, 5, etc.).

"And/or" means one or both. For example, the expression component A and/or component B refers to a component A alone, component B alone, or to both component A and component B.

Adding an "(s)" to a term means that the term is intended to include the singular and plural forms. For example, the term "additive(s)" refers to one additive as well as one or more additives (e.g., 2, 3, 4, etc.).

Unless otherwise indicated, all numbers expressing quantities of ingredients, measurement of physical properties such as described below and so forth used in the specification and claims are to be understood as being modified in all instances by the term "about."

The terms "comprise" or "contain," and variations thereof do not have a limiting meaning where these terms appear in the description and claims. The term "comprise" shall also include the terms "consist essentially of" and "consist of." "Consisting essentially of" means that specific further components can be present, namely those which do not materially affect the essential characteristic of the article or composition. "Consisting of" means that no further components should be present.

The dental restoration industry has long been interested in fabricating multi-layer zirconia milling blanks that yield, after sintering, a dental restoration that looks more like a natural tooth. In a natural tooth, color intensifies from the incisal end to the gingival end, while translucency increases in from the gingival end to the incisal end. As discussed above, previously known methods use layers of zirconia having different concentrations of colorant and yttria to approximate that appearance, such as described in U.S. Pat. No. 8,936,848 to Jung and U.S. Pat. No. 10,245,127 to Rolf et al.

As further noted above, however, those patents concern creating layers having different chemical composition, and do not address the practical issues in manufacturing such milling blanks. Because adjacent layers of blanks manufactured in accordance with previously known technologies have different chemistries, the mechanical properties of the layers also differ. In particular, the differential densification of the adjacent layers during sintering can lead to high internal stresses within the milling blank, which manifest as cracks in the milled dental restorations. FIGS. 1A and 1B, illustrate such cracking at the interface of adjacent layers in dental restorations prepared in accordance with the above-mentioned U.S. Pat. No. 8,936,848, rendering such processes esthetically unacceptable.

One previously known solution proposed to address the issue of abrupt change in mechanical properties at the interface of adjacent zirconia layers having widely different compositions is described in U.S. Pat. No. 10,898,302 to Dittman. That patent describes a technique using from seven to thirteen layers having alternating chemical compositions, with a goal of reducing the layer thicknesses beyond what is perceptible to the human eye. FIG. 2 is an illustrative example of a sintered material made in accordance with that patent. However, as will be observed in FIG. 2, there remain noticeable demarcations in color and translucency of the finished product that detract from the realism of the dental restoration.

FIG. 3 is an illustration of a sintered article made from a milling blank in which multiple layers of zirconia having different chemical compositions are layered on one another in accordance with previously known techniques, as discussed with respect to FIGS. 1 and 2. By comparison, FIG. 4 is an illustration of a sintered article made from a milling blank prepared in accordance with the present invention. For the sintered article of FIG. 4, multiple layers of zirconia having different chemical compositions first were layered on one another, as in FIG. 3, with the topmost exposed layer being textured using the inventive apparatus before the succeeding layer was deposited. Next, particles in the vicinity of the interface between the topmost adjacent layers were intermixed using the inventive apparatus.

As described in more detail below, the inventive apparatus includes a comb having a multiplicity of tines. The comb is reciprocated for at least one cycle to create a texture on each layer before deposition of the next adjacent layer of powder into the mold. When the mold is filled, the comb may be further reciprocated to penetrate the interface between upper adjacent layers of differently constituted zirconia powders to cause interleaving of those layers and to redistribute the particles near the interfaces. After sintering, a dental restoration made by the inventive process yields a natural-looking color and translucency gradient that closely approximates that of natural teeth. As can be observed comparing FIGS. 3 and 4, the color/translucency banding seen in FIG. 3 is greatly reduced, thus improving the mechanical as well as esthetic properties of the resulting dental restoration.

Figure 6:
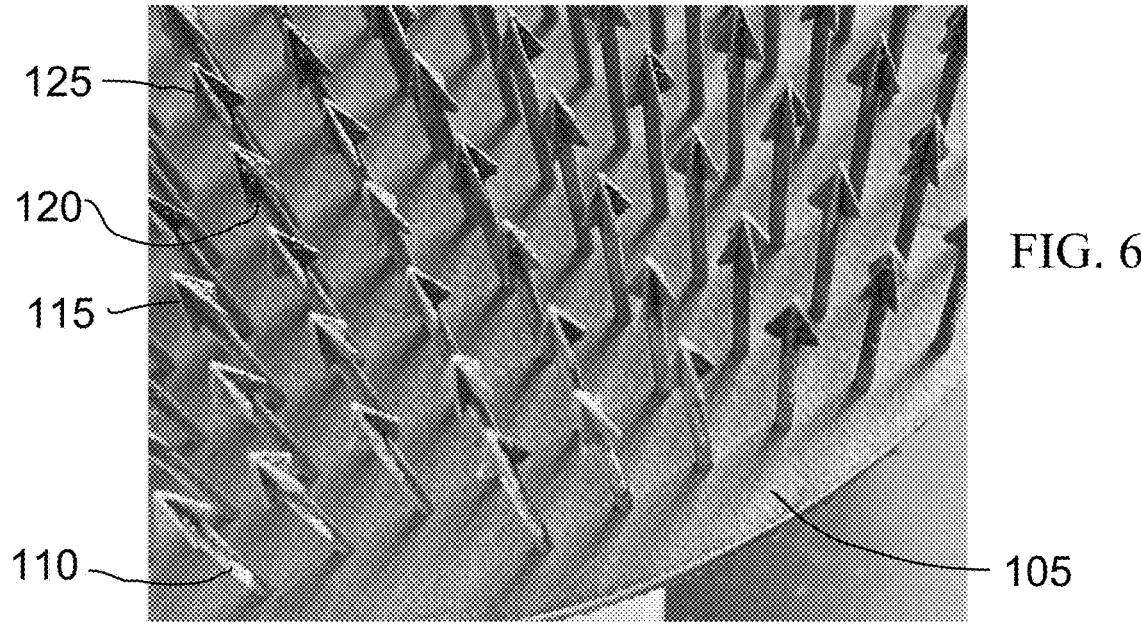
FIG. 6 is a detailed perspective view of the tines of the apparatus of FIG. 5.

Referring now to FIGS. 5 and 6, a preferred embodiment of the inventive apparatus is described. As depicted in FIG. 5, the inventive apparatus includes comb 100 having base 105 from which a multiplicity of tines 110 project. Base 105 may be coupled to a handle for manually operating the apparatus or alternatively may be coupled to an automated mechanism for industrial scale use. The multiplicity of tines 110 may be spaced apart at regular intervals over the entire area of base 105 and terminate at their extremities with shaped end portions 115. The length of tines 110 to the proximal end of the shaped end portion preferably is slightly longer than the depth of the upper layer of zirconia powder, as described herein below. Alternatively, if base 105 is coupled to a mechanically actuated arm, such as a robot, the length of tines 110 may be much longer, with the stroke of the arm being controlled by the mechanically actuated arm. As a further alternative, the tines 100 may be of different lengths over the area of comb 100 to cause greater or lesser amounts of interspersion of the particles at the zirconia interface.

In the embodiment of FIGS. 5 and 6, shaped end portions 115 of tines 110 have an arrow-type cruciform shape, similar to a broadhead arrow that consists of two triangles that are perpendicular to each other. Preferably, the shaped end portions are about 5 mm long and inserted into a powder layer surface, as described below, the full head penetrates the surface.

In accordance with one aspect of the invention, the proximal ends of shaped end portions 115 form shoulders 120 with tines 110. Accordingly, when comb 100 is advanced to cause tines 100 and shaped end portions 115 to penetrate through an interface formed by adjacent layers of zirconia powders having different chemical compositions, distal surfaces 125 of shaped end portions 115 push the upper layer of zirconia powder vertically downward into the lower layer of zirconia powder while simultaneously dragging material from the upper zirconia layer downward into the lower layer along shoulders 120. In this way, particles from the upper and lower zirconia layers may be interspersed to any desired amount to affect the color and translucency across the thickness of the milling blank, thereby attaining color and translucency gradients that mimic gingival to incisal gradients in natural teeth.

Comb 100 preferably is made of a sturdy hard plastic or metal, such that tines 110 and shaped end portions 115 remain firmly affixed to base 105, and permit reuse of comb 100 for manufacture of multiple milling blanks. Comb 100 preferably has a surface finish that is easily cleaned, e.g., using compressed air or by rinsing with an appropriate solvent, such as water, to ensure that particles do not adhere to tines 110 and shaped end portions 115.

Figures 7, 8A, 8B, 9A, 9B:
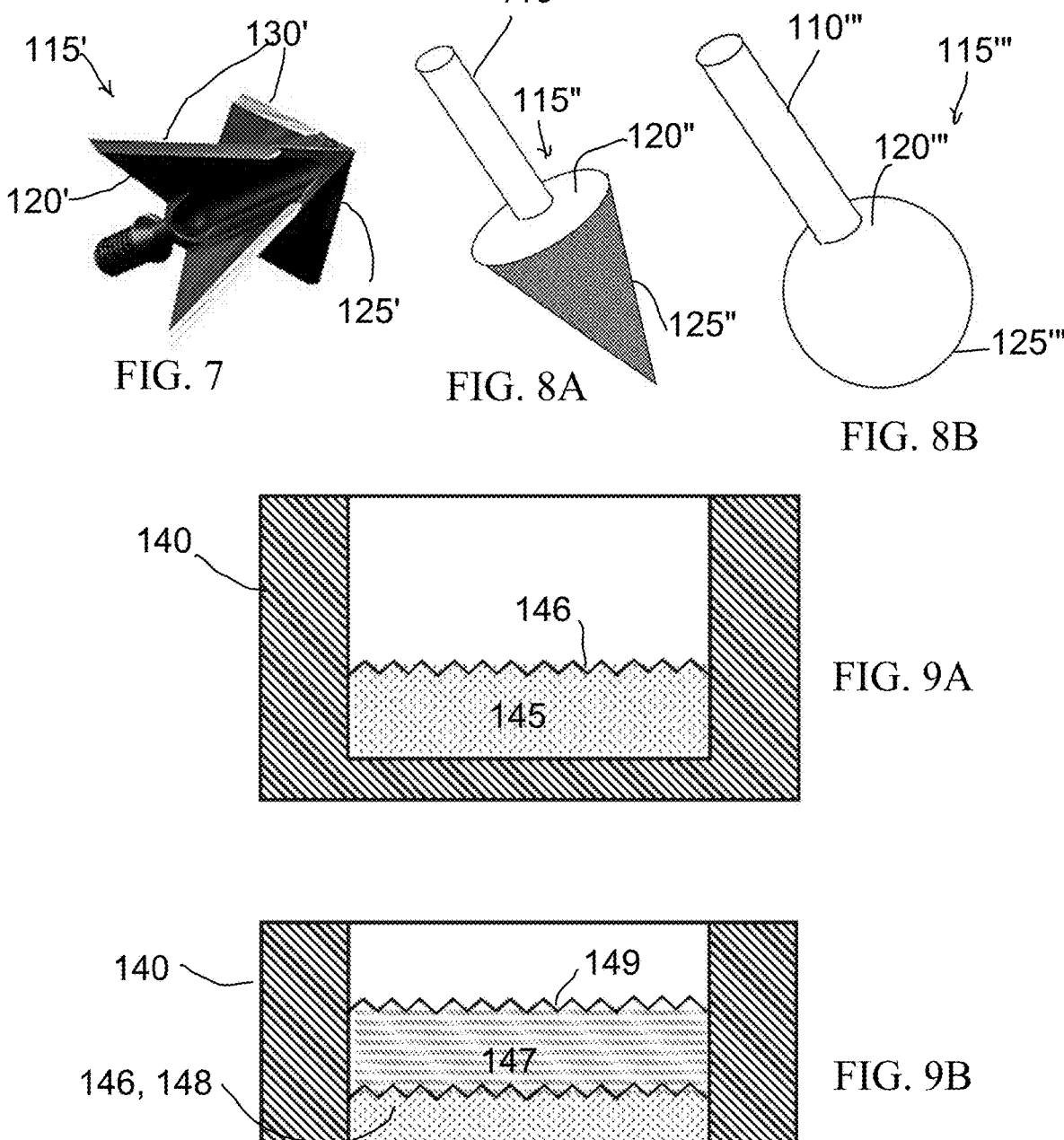
FIG. 7 is a detailed perspective view of an alternative embodiment of the cruciform-shaped end portion of a tine for use in the apparatus of FIG. 5.
FIGS. 8A and 8B are detailed perspective views of alternative shaped end portions suitable for use in the apparatus of the present invention.
FIGS. 9A and 9B depict side sectional views of an exemplary process of filling a mold with two layers of zirconia powder having different concentrations of yttria, in accordance with the methods of the present invention.

Referring now to FIGS. 7, 8A and 8B, alternative designs of shaped end portions for use with tines 110 of comb 100 are described. In FIG. 7A, arrow-shaped cruciform shaped end portion 115' includes sharpened edges 130' along distal surface 125' to facilitate penetration into the layers of zirconia powder. In FIG. 8A, shaped end portion 115" is in the form of a solid cone, which provides a more pronounced shoulder 120" with tine 110" designed to carry particles from the upper layer of zirconia powder vertically downward into the lower layer of zirconia powder. In FIG. 8C, tine 110''' terminates in bulbous shaped end portion 115''' having distal surface 125''' expected to push a greater volume of particles downward and having a less pronounced shoulder 120''' to drag particles from the upper layer of zirconia powder behind it. Shaped end portion advantageously may include other forms, such as bulbous or hook shaped.

Turning to FIGS. 9 and 10, methods of using comb 110 of the present invention are now described. FIG. 9A is a side sectional view of milling blank mold 140 in which a first, lower layer 145 of a zirconia powder has been deposited. Milling blank mold 140 may be a conventional milling blank mold having a cavity with thickness in a z-direction and an area in an x/y-plane normal to the z-direction. For producing dental milling blocks, the volume of the cavity of the mold is typically in a range of 2 to 2,000 ml or 5 to 500 ml or 10 to 300 ml.

During a milling blank creation process, first layer 145 of a zirconia powder having a first concentration of yttria, and optionally, a first concentration of a colorant, is deposited in the mold cavity to a first desired thickness. The filling of the powder into mold 140 may be done with various conventional equipment, including a vibration feeder, screw feeder or by using a fill shoe. Top surface 146 of first layer 145 may be leveled, e.g., using a spatula, or by slight compression or agitation. In accordance with one aspect of the invention, the comb is then reciprocated to penetrate top surface 146 of layer 145, e.g., to a depth of about 5 mm, to create a regular textured pattern, e.g., a multiplicity of dimples corresponding to the multiplicity of tines, in top surface 146 (indicated by zigzag, which is actually a three-dimensional pattern across the x-y area of mold 140).

This process is repeated for the next layer of zirconia powder, as depicted in FIG. 9B. In particular, second layer 147 of zirconia powder having a second concentration of yttria, and optionally, a second concentration of colorant than layer 145 is deposited in mold 140 on top surface 146 of first layer 145 to a desired thickness. In this case, top surface 146 of first layer 145 and a bottom surface of second layer 147 form complimentary interface 148 having the textured pattern previously formed by comb 100 on surface 146. Top surface 149 of second layer 147 also may be leveled using a spatula, compression or agitation and then textured by reciprocating comb 100. As depicted in FIG. 9B, in a preferred embodiment, first layer 145 and second layer 147 typically are parallel to each other and the interior base of mold 140. In the embodiment illustrated in FIGS. 9A and 9B, two different zirconia powders compositions are used, but it is intended that the above-described process of filling mold 140 with multiple layers having textured interfaces may be used for any number of desired layers of zirconia. As further described below, after filling of mold 140 is completed, comb 100 may be reciprocated through two or more of the uppermost zirconia layers to further intersperse particles at the interfaces between adjacent layers.

As will be readily understood, the zirconia powders used to form first layer 145 and second layer 147 differ from each other with respect to their physical properties and/or chemical composition and/or color. The chemical composition may affect the coloration and translucency of the sintered product. For example, the powders may differ from each other with respect to concentration of a single colorant, by using a different coloring components, or by using a mixture of both. The zirconia powders also may comprise ceramic components and stabilizing components and differ from each other with respect to the content of the stabilizing components. Importantly, the zirconia powders used in the various layers deposited in mold 140 should be fabricated to have appropriately matched mechanical properties, with respect to, for example, densification and thermal expansion/contraction coefficients. Zirconia powders commercially available from Tosoh Company, Japan, advantageously may be used with the processes described herein, for example, where the incisal layer of the milling blank is made from Zpex® Smile zirconia powder and the gingival layer is made from Zpex4™ zirconia powder.

Figure 10A:
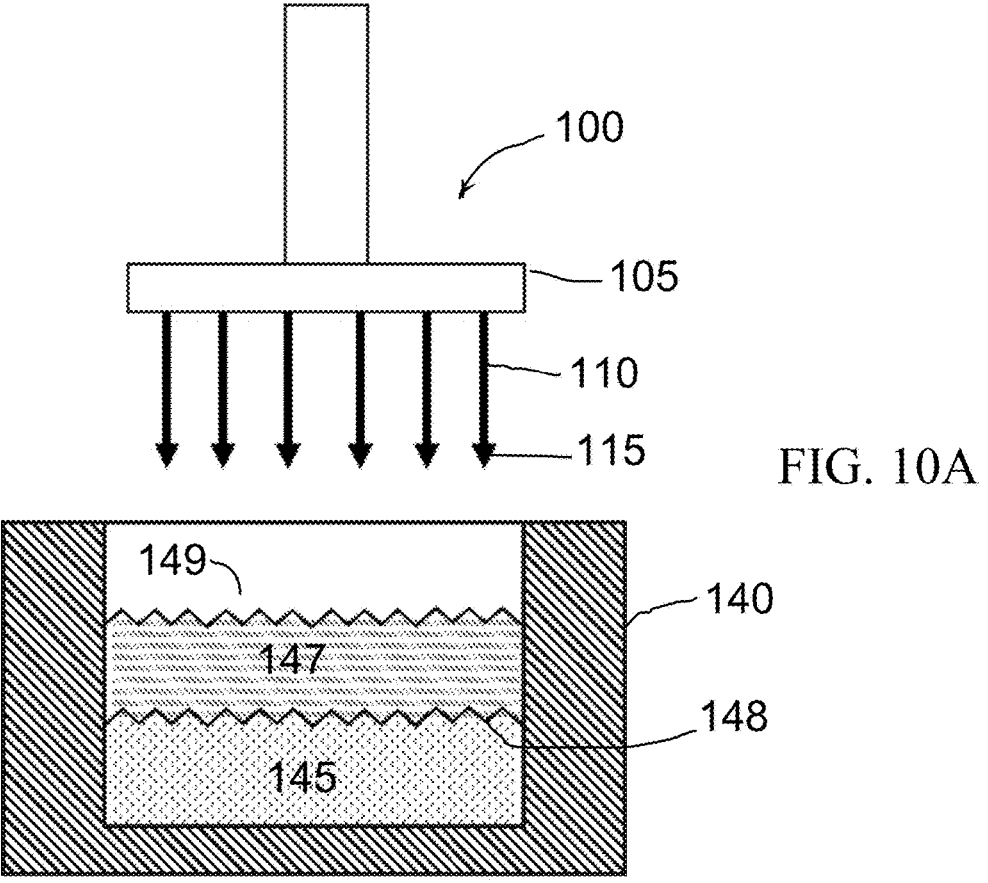
FIGS. 10A to 10C depict side sectional views illustrating the method of interspersing differently constituted zirconia powders in the vicinity of the interface between adjacent layers in accordance with the present invention.
Figure 10B:
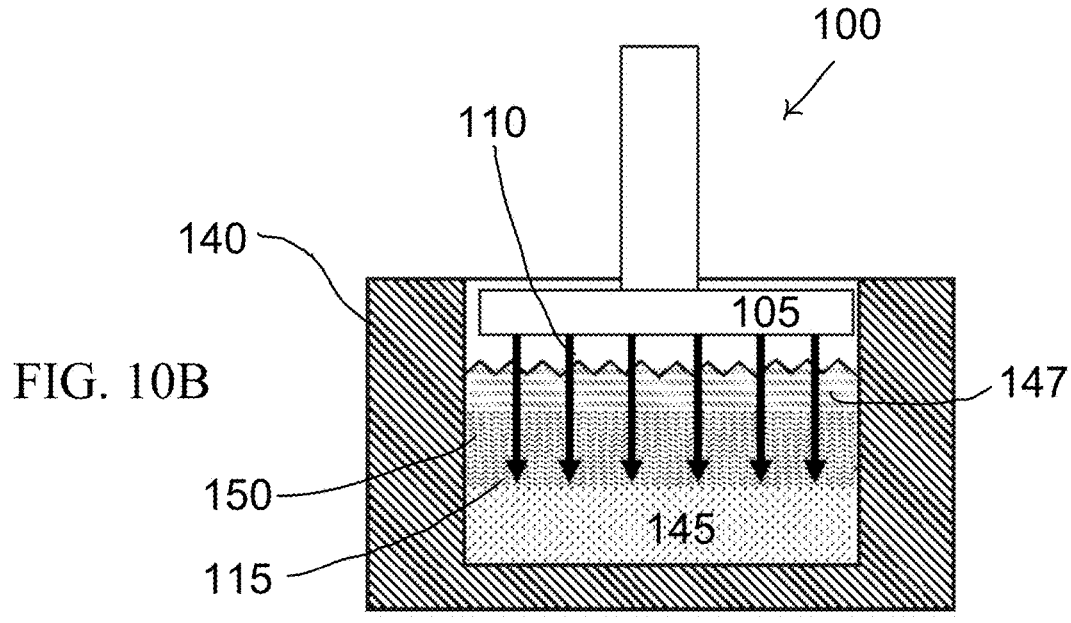
Figure 10C:
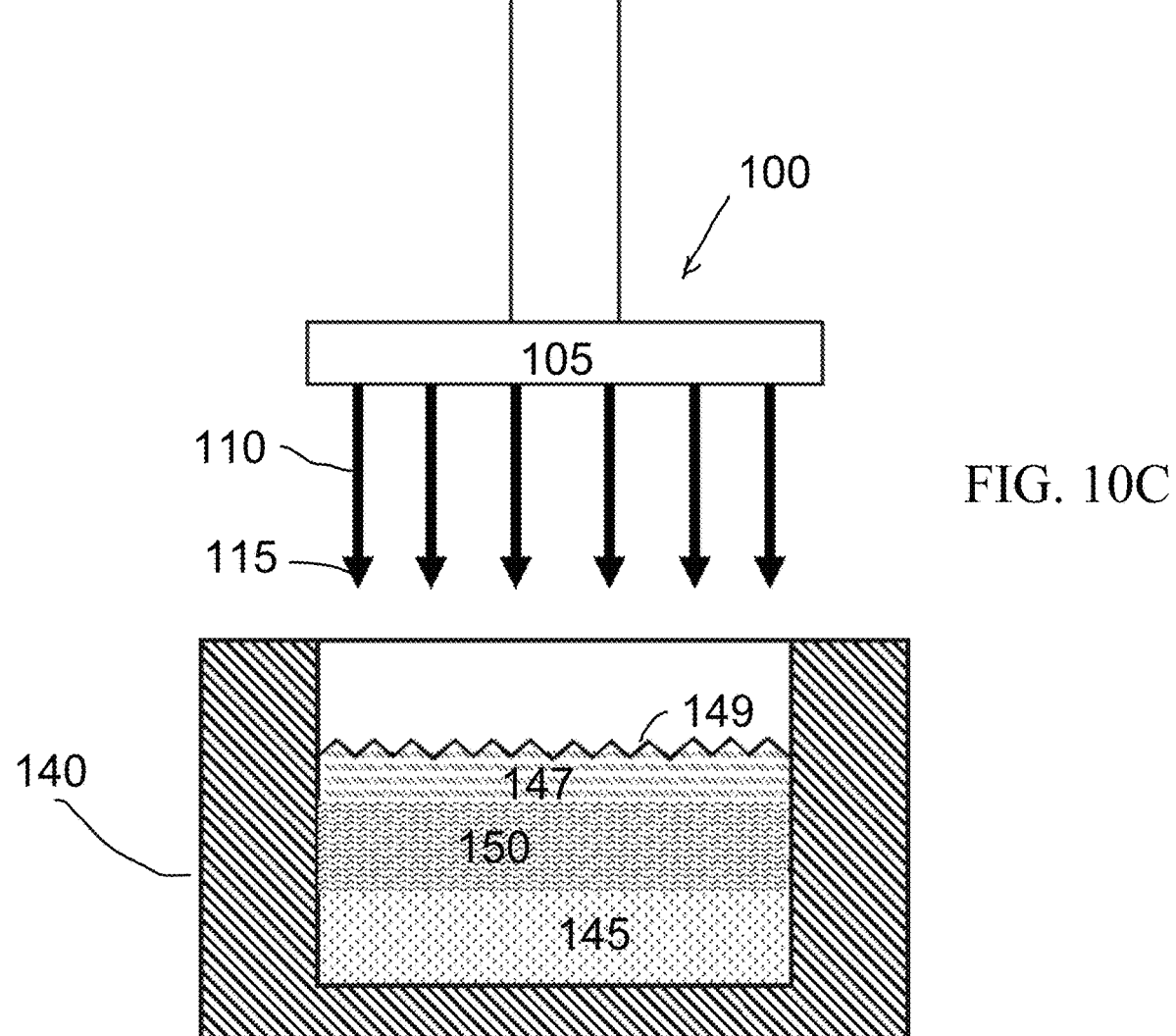

Compaction and sintering of the multiple layers depicted in without the texturing process of the present invention, as illustrated in FIG. 9B, will result in a sintered product having a distinct difference in color and/or translucency at interface 148, as illustrated in FIGS. 1 to 3 above. Referring now to FIGS. 10A to 10C, a further aspect of preparing a milling blank using the inventive apparatus is described. In particular, after mold 140 is filled as described with respect to FIGS. 9A and 9B, comb 100 is arranged vertically above mold 140 having multiple layers with textured interfaces, as depicted in FIG. 10A. Further in accordance with the invention, as depicted in FIG. 10B, comb 100 is inserted vertically downward into mold 140 to the penetrate interface 148 and then withdrawn, thereby intermixing the particles of the respective powders to create interface region 150.

The step of inserting and retracting comb 100 may be conducted a single cycle, or repeated for a number of cycles, with the insertion depth of comb 100 for each penetration depth into interface region 150 being the same, or more preferably, shallower during successive cycles. In this manner, it may be possible to redistribute the powders to a lesser extent relative to the original interface during each subsequent cycle through interface region 150. Alternatively, after comb 100 is retracted at conclusion of a single penetration cycle, comb 100 may be rotated circumferentially 90 degrees relative to mold 140 and inserted again to more thoroughly circumferential distribute interspersion of the particles in interface region 150. Once this process is completed, as depicted in FIG. 10C, comb 100 may be removed. Mold 140 then is subjected to further isostatic compression and sintered to form a milling blank from which dental restorations may be prepared.

Powders suitable for use in producing the dental milling blanks having desirable mechanical and esthetic properties are characterized as follows a $ZrO_2$ content of 70 to 98 mol % or 90 to 98 mol % and $Y_2O_3$ content of 3 to 7 mol %. A higher yttria content typically leads to an increase of the cubic crystal phase in the zirconia ceramic material after sintering the material to final density. A higher content of the cubic crystal phase may contribute to a better or higher translucency. In some embodiments the material of the porous dental zirconia article contains about 3, 4 or 5 mol % yttria. It has been found that these materials are particularly useful for producing an aesthetic zirconia dental restoration in a firing process as described in the present text. For producing the dental milling blank described herein at least two powders are used which differ from each other with respect to chemical composition and/or color, the respective powders may differ from each other with respect to yttria content and/or amount or nature of coloring components. At least one zirconia powder, e.g., used for the gingival portion of the milling blank has an yttria content being lower than the yttria content of zirconia powder used in the incisal portion of the blank. After sintering, the respective compositions will have different translucencies, with the higher yttria content being typically more translucent than the region with the lower yttria content. For producing the dental milling block described herein, the first and the second powders may differ from each other at least with respect to the amounts of stabilizing components and/or coloring components being present in the respective powder.

For preparation of a milling blank having more than two layers, creation of the textured pattern at the interface of adjacent layers during the mold filling process may be sufficient to provide an esthetic transition in the gingival region, while the uppermost incisal layers of the milling blank generally will exhibit a more esthetic and natural translucency gradient by more widely interspersing particles from adjacent zirconia layers by reciprocating the comb through the layer interface to greater an interface region, as described with respect to FIG. 10A to 10C. For example, using the inventive comb is expected to be sufficient for the texture patterned interfaces between the first four gingival layers of a five-layer milling blank, with the addition of reciprocating the tines of the comb fully through the fifth layer of zirconia powder, although this may vary depending upon the desired color shade and translucency of the existing teeth to be matched by the dental restoration. Following the mold filling and processing, as described above, the mold may be compacted and sintered according to conventional dental blank manufacturing processes.

Certain modifications and improvements will occur to those skilled in the art upon reading the foregoing description. The above-mentioned embodiments are provided to serve the purpose of clarifying the aspects of the invention and it will be apparent to one skilled in the art that they do not serve to limit the scope of the invention.

What is claimed is:

1. A process of manufacturing a dental milling block having a translucency and/or color gradient, the process comprising:

providing a mold with a cavity having a z-direction and defining an area in a x/y-plane;

providing a comb having a base extending in the x/y plane and a multiplicity of tines projecting vertically from the base in the z-direction, each one of the multiplicity of tines consisting of an elongated rod having a first diameter, a proximal end coupled to the base and a distal region adjacent to a distal end, the distal region having a second diameter substantially larger than the first diameter to form a shoulder;

partially filling the cavity with a first zirconia powder to form a first layer having a top surface;

reciprocating the comb into the mold only in the z-direction to penetrate the top surface of the first layer and create a textured pattern in the top surface of the first layer;

introducing into the mold a second zirconia powder on top of the first layer of first zirconia powder to form a second layer having a top surface and a bottom surface, the textured pattern in the top surface of the first layer creating a complimentary textured pattern in the bottom surface of the second layer, the textured pattern in the top surface of the first layer and the complimentary textured pattern in the bottom surface of the second layer together forming a first interface;

reciprocating the comb into the mold only in the z-direction to penetrate the second layer and the first interface, such that the shoulder of each tine carries particles from the first layer upwards into the second layer when the comb is retracted through the second layer; and compacting the first and second layers in the mold and optionally applying heat to the compacted first and second layers, wherein the first zirconia powder has different chemical composition and/or color than the second zirconia powder.

2. The process according to claim 1, wherein retracting the comb through the second layer creates a textured pattern in the top surface of the second layer, the process further comprising, prior to compacting the first and second layers in the mold:

depositing a third layer of a third zirconia powder on top of the second zirconia powder to form a third layer having a top surface and a bottom surface, the textured pattern in the top surface of the second layer creating a complimentary textured pattern in the bottom surface of the third layer, the textured pattern in the top surface of the second layer and the complimentary textured pattern in the bottom surface of the third layer together forming a second interface;

wherein the third zirconia powder has a chemical composition different than the first and second zirconia powders.

3. The process of claim 2, further comprising, prior to compacting the first and second layers in the mold:

reciprocating the comb into the mold only in the z-direction to penetrate the third layer and the second interface, such that the shoulder of each tine carries particles of the second zirconia powder upwards into the third layer.

4. The process of claim 3, wherein the comb is reciprocated for several cycles into the mold in the z-direction to intermix particles from the first, second and third layers, wherein each depth of penetration is progressively shallower with each succeeding cycle.

5. A process of producing a dental restoration comprising:

manufacturing a dental milling block according to the process of claim 1;

applying heat to the compacted first and second layers to obtain a heat-treated dental milling block;

machining a dental restoration from the heat-treated dental milling block; and sintering the dental restoration.

6. A process of manufacturing a dental milling block having a translucency and/or color gradient, the process comprising steps of:

providing a mold with a cavity having a z-direction and defining an area in a x/y-plane;

providing a comb having a base extending in the x/y plane and a multiplicity of tines projecting vertically from the base in the z-direction, each one of the multiplicity of tines consisting of an elongated rod having a first diameter, a proximal end coupled to the base and a distal region adjacent to a distal end, the distal region having a second diameter substantially larger than the first diameter to form a shoulder;

depositing a zirconia powder into the mold to form a layer having an upper surface;

reciprocating the comb into the mold only in the z-direction to create a textured pattern in the upper surface;

depositing a subsequent layer of a different zirconia powder into the mold on top of the textured pattern in the upper surface, the subsequent layer having an upper surface and a bottom surface with a complimentary textured pattern, the textured pattern and complimentary textured pattern together forming an interface;

reciprocating the comb into the mold only in the z-direction to penetrate the subsequent layer and the interface, such that the shoulder of each tine carries particles from the layer upwards into the subsequent layer when the comb is retracted through the subsequent layer;

repeating the steps of reciprocating the comb and depositing another subsequent layer of a different zirconia powder to form multiple adjacent layers of different zirconia powders having multiple interfaces; and compacting the multiple adjacent layers in the mold and optionally applying heat to the compacted multiple adjacent layers.

7. The process according to claim 6, further comprising, prior to compacting the multiple adjacent layers in the mold:

reciprocating the comb into the mold only in the z-direction to penetrate at least two uppermost adjacent layers of the multiple adjacent layers such that the shoulder of each tine intersperses particles of the different zirconia powders to create an interface region.

8. The process according to claim 7, wherein the comb is reciprocated for several cycles into the mold in the z-direction to create the interface region, wherein each depth of penetration through the interface region is progressively shallower with each succeeding cycle.

9. A process of producing a dental restoration comprising:

manufacturing a dental milling block according to the process of claim 6;

applying heat to the compacted multiple adjacent layers to obtain a heat-treated dental milling block;

machining a dental restoration from the heat-treated dental milling block; and sintering the dental restoration.

10. The process for manufacturing a dental milling block according to claim 1, wherein providing the comb comprises providing a comb in which the distal region has a cruciform shape.

11. The process for manufacturing a dental milling block according to claim 10, wherein providing the comb comprises providing a comb in which the cruciform shape comprises intersecting triangles, wherein proximal surfaces of the intersecting triangles form the shoulder.

12. The process for manufacturing a dental milling block according to claim 1, wherein providing the comb comprises providing a comb in which each distal region comprises a cone, a flat base of the cone forming the shoulder where the distal region is coupled to the elongated rod.

13. The process for manufacturing a dental milling block according to claim 1, wherein providing the comb comprises providing a comb in which each distal region is spherical.

14. The process for manufacturing a dental milling block according to claim 1, wherein providing the comb comprises providing a comb in which each distal region has a length of about 5 mm.

15. The process for manufacturing a dental milling block according to claim 1, wherein providing the comb comprises providing a comb in which the base is coupled to a handle.

16. The process for manufacturing a dental milling block according to claim 1, wherein providing the comb comprises providing a comb coupled to a mechanically actuated arm.

17. The process for manufacturing a dental milling block according to claim 16, wherein reciprocating the comb comprises reciprocating the comb using the mechanically actuated arm.

\* \* \* \* \*